United States Patent [19]

Kiwak

[11] 4,314,566
[45] Feb. 9, 1982

[54] AIR COOLER FOR SELF-CONTAINED BREATHING SYSTEM

[75] Inventor: Robert S. Kiwak, Northville, Mich.

[73] Assignee: The Bendix Corporation, Southfield, Mich.

[21] Appl. No.: 182,204

[22] Filed: Aug. 28, 1980

[51] Int. Cl.³ .............................................. A62B 7/00
[52] U.S. Cl. .......................... 128/204.15; 128/202.26; 165/104.21; 62/333
[58] Field of Search ..................... 128/201.25, 204.15, 128/202.26; 165/105; 62/333

[56] References Cited

U.S. PATENT DOCUMENTS

| | | | |
|---|---|---|---|
| 3,828,849 | 8/1974 | Corman et al. | 165/105 |
| 3,850,001 | 11/1974 | Locke | 165/105 |
| 4,186,735 | 2/1980 | Henneman et al. | 128/201.25 |

*Primary Examiner*—Henry J. Recla
*Attorney, Agent, or Firm*—W. G. Christoforo; Bruce L. Lamb

[57] ABSTRACT

A heat exchanger for cooling the recycled air of a self-contained closed loop breathing apparatus having a tank of high pressure breathable gas such as oxygen includes a heat sink located inside the tank, a heat exchange element located outside the tank in the stream of recycled air, and a heat pipe extending through one end closure of the tank providing heat communication between the heat exchanger element and said heat sink.

5 Claims, 3 Drawing Figures

AIR COOLER FOR SELF-CONTAINED BREATHING SYSTEM

BACKGROUND OF THE INVENTION

This invention relates to a breathing apparatus and more particularly to a heat exchanger for use in a closed loop breathing apparatus for cooling the recycled gas.

Breathing apparatuses are generally of the open loop or the closed loop type. In the open loop type, compressed gas is delivered to the user and expired gas is vented to the atmosphere. Such systems are relatively simple and have the advantage of providing cool breathing gas to the user with a minimum of breathing resistance. However, since the gas is not recycled, a portable open loop breathing apparatus of reasonable weight has a relatively small supply of breathable gas available. In a closed loop breathing apparatus the exhaled gases are directed through a device which generates oxygen or at least removes carbon dioxide from the gas, which is then recycled to the user. Although some high pressure gas is normally supplied to the recycled gas, the high pressure gas tank can be relatively small and lightweight and still provide a breathing system which has a relatively long duration of air supply. Closed loop breathing apparatus systems, however, have the disadvantage that there is a significant buildup of heat in the recycled gas so that some means must be provided to remove at least a portion of the heat to make use of the system relatively move comfortable.

Prior art systems have provided a heat exchanger in the form of a jacket, coils or other means surrounding the high pressure gas tank and through which the recycled gas is passed in intimate contact with the exterior surface of the gas tank. As is well known, the flow of high pressure gas from the high pressure gas tank causes cooling of the tank so that there is a heat flow from the recycled gas to the tank through the heat exchanger. This type of heat exchanger permits only relatively slow heat flow so that the recycled air remains relatively warm.

SUMMARY OF THE INVENTION

The present invention permits more effective use of the high pressure tank as a heat sink thus allowing faster heat flow and a cooler, more comfortable breathable gas. The present invention comprises dual heat exchanger elements, a heat sink element located inside the high pressure tank and a gas cooler element located external thereto, connected by a heat pipe. The heated recycled gas is passed through the external heat exchanger element. The other heat exchanger element, being inside the high pressure tank, efficiently transfers its heat to the high pressure gas therein. The heat pipe provides efficient means for rapidly transferring heat from the external heat exchanger element to the internal heat exchanger element whereby the recycled gas is rapidly cooled to a more comfortable temperature.

The main advantage of this invention is that it permits more effective use to be made of the heat sinking ability of the gas in the high pressure tank of an operating closed loop breathing apparatus in cooling the recycled gas.

DESCRIPTION OF THE PREFERRED EMBODIMENT

Figure 1:
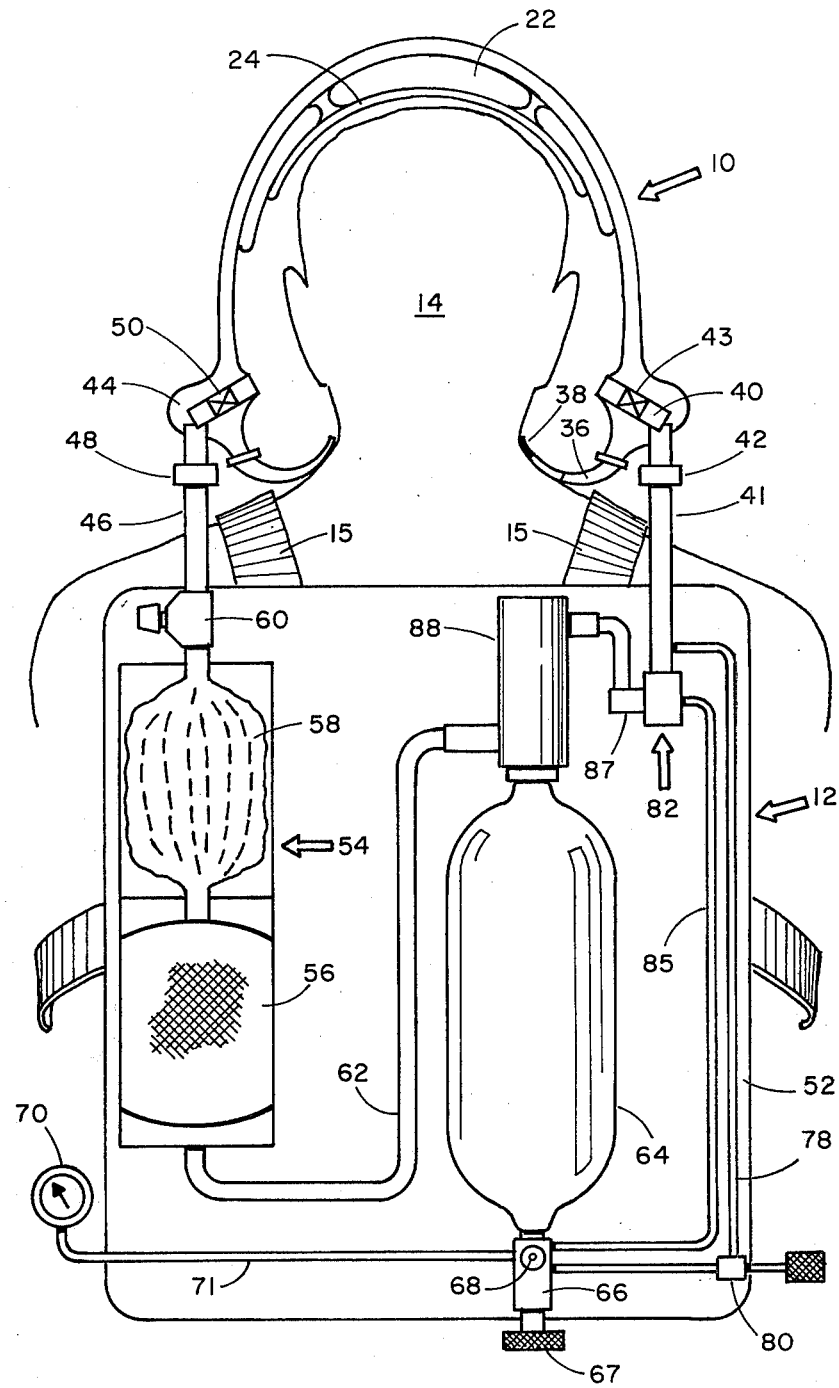
FIG. 1 is a somewhat schematic view of a typical portable closed loop breathing apparatus in use by a wearer.

A typical portable breathing apparatus in which the invention is used is illustrated in FIG. 1 and includes a helmet, indicated in its entirety by the numeral 10, and a backpack, indicated in its entirety by the numeral 12, the helmet being adapted for mounting over the head of the user or wearer 14, while the backpack is supported on the back of the wearer by means of shoulder straps 15. Except for the use of the heat exchanger of the present invention, indicated by the numeral 88, the illustrated breathing apparatus is well known in the art and is generally of the type fully described in U.S. Pat. No. 4,186,735. Briefly, helmet 10 includes padding 22 and 24 for the comfort of the wearer and an annular flexible neck seal 36 which seals the helmet to the neck of the wearer.

A helmet inlet port 40 is connected to an inlet breathing line 41, suitably by means of a quick disconnect device 42 of conventional construction. An inlet check valve 43 is disposed in inlet port 40 to permit movement of gas only into the interior of the helmet. An exhaust port 44 is disposed on the opposite side of the helmet from inlet port 40 and is connected to an exhaust breathing line 46, suitably by means of a quick disconnect device 48. The exhaust port is provided with a check valve 50 that permits movement of gas only from the helmet interior.

Backpack 12 includes rigid housing 52 which protects the backpack contents. Mounted in the housing is a carbon dioxide scrubbing device indicated by numeral 54 which includes a pack of carbon dioxide absorbing materials 56. Alternately, a material could be provided in place of a carbon dioxide scrubbing device that chemically converts carbon dioxide to oxygen, such as potassium superoxide. A breathing bag of exhaust gas reservoir 58 is disposed in scrubbing device 54 between carbon dioxide absorbing material 56 and exhaust breathing line 46 to supply exhaust gas to the scrubbing device when the breathing apparatus operates, the breathing bag being flexible and filling with gas as the wearer exhales. A relief valve 60 is provided in the exhaust breathing line 46 at the inlet of the breathing bag 58 and vents gas to the atmosphere when the exhaust gas exceeds the capacity of the scrubbing device and results in back pressure in the exhaust breathing line. The scrubbed gas is delivered to an outlet line 62 at the bottom of scrubbing device 54.

An oxygen cylinder 64 is mounted in housing 52 adjacent the scrubbing device and is inverted so that its outlet is adjacent the bottom of the housing. A pressure reducer 66 is mounted on the outlet of the oxygen cylinder. An on-off valve is associated with the pressure reducer and is controlled by a knot 67 extending through the bottom of housing 52. Also associated with the pressure reducer is a fill port 68 for recharging the oxygen cylinder and a pressure gage 70 that is disposed on the exterior of housing 52 and connected to the oxygen cylinder by line 71.

A bypass line 78 extends between the pressure reducer and breathing line 41, and a bypass valve 80 controls the flow through line 78, the valve being actuated by a knob on the exterior of the housing so that the wearer can selectively open the valve to permit oxygen flow directly from the regulator to the breathing line in the event a malfunction obstructs the normal flow to the breathing line.

A regulator valve 82 is mounted in the housing adjacent the upper end of oxygen cylinder 64. The regulator valve includes a valve body having an oxygen supply inlet which is connected to the outlet of pressure reducer 66 by an oxygen supply line 85. The regulator valve has a second inlet connected to an inlet line 87 that is connected in turn to the outlet line 62 of the scrubber device 54 through a heat exchanger 88 which is shown in greater detail below. The regulator valve controls the addition of oxygen from line 85 with the recycled gas from line 87 and supplies the resulting mixture to the helmet interior at the demand of the wearer through line 41.

Figure 2:
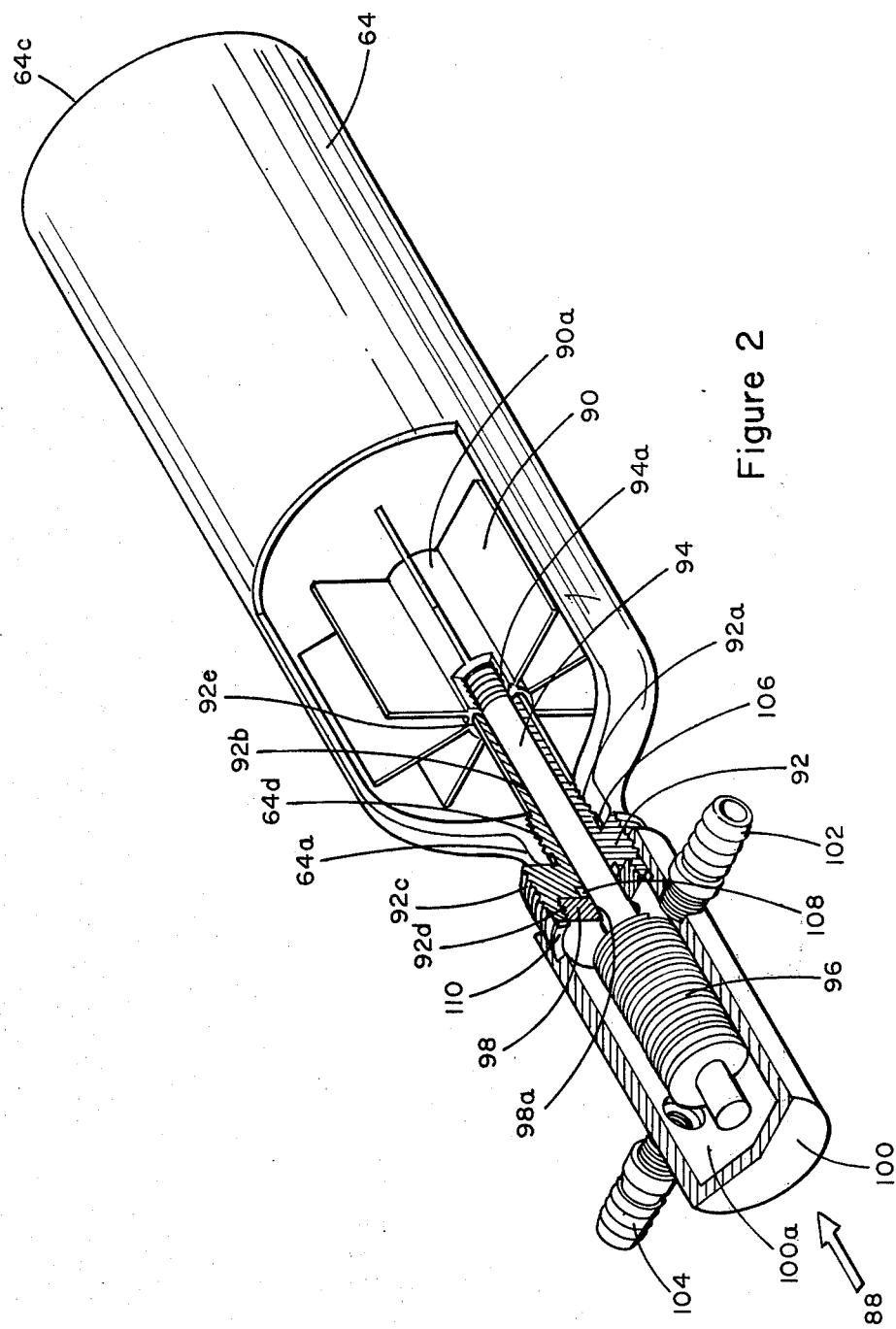
FIG. 2 is a cut-away isometric view of a partially manufactured high pressure gas storage tank having a heat exchanger according to the present invention.

Refer now to FIG. 2 which shows a partially manufactured oxygen cylinder 64 assembled together with heat exchanger 88. Cylinder 64 is manufactured from a single piece of aluminum tubing which is spun down on one end to form neck 64a having internal pipe threads 64d. Cylinder end 64c, opposite neck 64a, will eventually be spun down and threaded to be similar to neck 64a but first heat sink element 90 will be installed inside cylinder 64 as will be explained below.

Heat exchanger 88 is comprised of fitting spacer 92 having an external thread 92a which is screwed onto thread 64d of neck 64a, an internal bore 92b, a second external thread 92c and an internal thread 92d. An O-ring seal 106 is provided between fitting spacer 92 and neck 64a. A heat pipe 94, which will be discussed more fully below, is fitted with a gas cooler element in the form of a spiral baffle 96 at one end and threaded at opposite end 94a. Heat pipe 94 is installed through bore 92b and threaded at end 94a into a thread in boss 90a of heat sink 90 until the boss pulls up tightly against shoulder 92e. A back-up stud 98 having bore 98a is screwed into thread 92d so as to compress O-ring 108 to thereby hold heat pipe 94 in place against longitudinal movement and also to provide a gas tight seal. A housing 100 is then assembled to fitting spacer 92 with a gasket 110 compressed therebetween to form a gas tight seal and hermetic chamber 100a.

Housing 100 includes ports 102 and 104 for gas input and outlet. With heat sink 90 securely in place in cylinder 64 end 64c is spun down to form a threaded neck similar to neck 64a for receiving pressure reducer 66 of FIG. 1.

Figure 3:
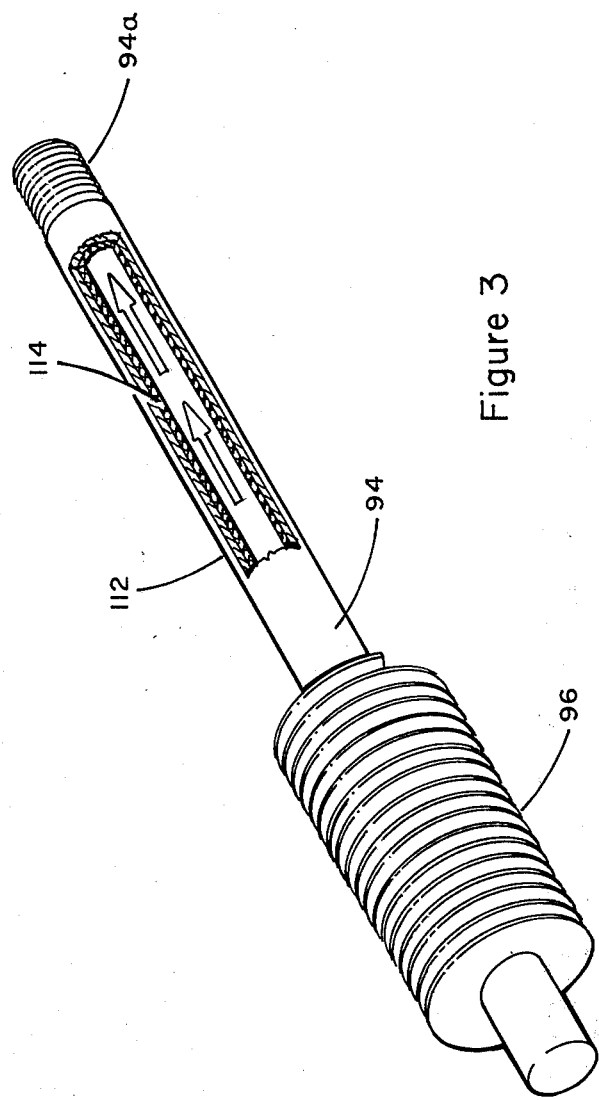
FIG. 3 is a cut-away view of a typical heat pipe.

Refer now to FIG. 3 which shows heat pipe 94 cut away to show its internal construction and spiral baffle 96 brazed or soldered thereto. The heat pipe is comprised of hard drawn copper tubing, closed at both ends so as to be hermetically sealed. Air is evacuated and the pipe partially back filled with a suitable liquid, such as freon 114 or 22, which boils at low temperatures. A wick material 114 is provided as an internal lining in the present embodiment where liquid freon must be moved against gravity by the wick. In those embodiments where the orientation of the heat pipe is such as to cause the liquid freon to be moved by gravity, the wick material might be omitted. The mode of operation of a heat pipe is quite simple but effective in rapidly conducting heat. Heat absorbed by spiral baffle 96 causes the liquid in the heat pipe to boil and vaporize. The vapor moves in the direction of the arrows to end 94a, which it will be remembered is attached to heat sink 90 inside the oxygen cylinder. Here the vapor is condensed, giving up its heat to the heat sink and thus to the oxygen contained in cylinder 64. The liquid is then transported back to the opposite end of the heat pipe by wick material 114. Suitable heat pipes are manufactured by Heat Pipe Corporation of America, 141 Park Place, Watchung, N.J.

The invention claimed is:

1. In a breathing apparatus having means for scrubbing carbon dioxide from a stream of gas exhaled by a user to provide a stream of recycled gas, a tank of compressed breathable gas and means for reducing the pressure of said compressed breathable gas and adding the reduced pressure gas to the stream of recycled gas for use by said user, a heat exchanger for cooling said stream of recycled gas comprising:

a heat sink located inside said tank;

a heat exchange element located outside said tank in said stream of recycled gas; and a heat pipe connecting said heat sink and said heat exchanger element.

2. The apparatus of claim 1 wherein said heat pipe comprises an elongated structure enclosing a hermetically sealed chamber from which air has been evacuated and back-filled with a relatively low boiling point liquid.

3. The apparatus of claim 2 wherein said low boiling point liquid comprises freon.

4. A self-contained closed loop portable breathing apparatus for recycling air exhaled by a user for reuse by said user by at least cooling the exhaled air and adding fresh breathable gas thereo, said apparatus including regulator means for receiving and mixing said fresh breathable gas and the cooled air and for supplying the resultant mixture to said user for reuse, a gas pressure reducer for reducing the pressure of a pressurized gas flowing therethrough to thereby produce said fresh breathable gas, and conduit means communicating said fresh breathable gas to said regulator means, comprising:

a source of said pressurized gas comprising a cylindrical double ended tank having said gas pressure reducer mounted on one end thereof, and an opposite end;

heat exchanger means mounted on said opposite end and comprising a heat sink located inside said tank, a heat exchanger element located outside said tank, and a heat pipe extending through said tank at said opposite end and connecting said heat exchanger element with said heat sink; and means communicating air exhaled by said user with said regulator means, said heat exchanger element being disposed therein whereby said air exhaled by said user is cooled.

5. The apparatus of claim 4 includes means hermetically sealing said heat pipe to said tank.

* * * * *